United States Patent [19]
Kang et al.

[11] Patent Number: 6,008,320
[45] Date of Patent: Dec. 28, 1999

[54] ELASTASE INHIBITOR AND PROCESS FOR PREPARING THE SAME

[75] Inventors: Ke-Won Kang; Hyo-Il Jung; Seok-Jin Hong, all of Taejon; Dong-Ryoung Kim, Seochun-Kun; Ju-Yun Lee, Taejon, all of Rep. of Korea

[73] Assignee: Korea Advanced Institute of Science and Technology, Taejon, Rep. of Korea

[21] Appl. No.: 09/130,121

[22] Filed: Aug. 6, 1998

Related U.S. Application Data

[63] Continuation of application No. 08/522,786, Sep. 1, 1995, abandoned.

[30] Foreign Application Priority Data

Apr. 27, 1995 [KR] Rep. of Korea ............... 95-10206

[51] Int. Cl.$^6$ .................................................. C07K 14/00
[52] U.S. Cl. ................... 530/324; 530/350; 530/325; 530/334
[58] Field of Search .................. 530/350, 324, 530/325, 334

[56] References Cited

U.S. PATENT DOCUMENTS 5,472,942  12/1995  Sawyer et al. ........................... 514/12

OTHER PUBLICATIONS

Jung et al, Chem. Abs., vol. 123, 221499 (1995) [J. Biol. Chem. vol. 270 (23), pp. 13879–13884 (1995)].
Lee et al, Chem. Abs., vol. 119, 2103582 (1993) [Han'guk Saenghwa Hakkoedn].
Wiedow et al, The Journal of Biol. Chemistry, vol. 265 (25) (Sep. 5, 1990), pp. 14791–14795.
Hochstrassen et al, Hoppe–Seyler's Z. Physiol. Chem., Bd. 362 S. 1369–75, (Oct. 1981).
Sollner et al, Eur. J. Biochem., vol. 219, pp. 937–943, (1994).
Lammers et al, British J. of Dermatology, vol. 115, pp. 181–186, (1986).
Seemuller et al, Hoppe Seyler's Z. Physiol. Chem. Bd. 35i, 1841–1846, (Dec. 1980).
Potempa, J. et al. An Elastase Inhibitor from Equine Leukocyte Cytosol Belongs to the Serpin Superfamily: . . . , J. Biol.Chem., 263(15): 7364–73699 (1988).
Frommherz, K.J. et al. Heparin Strongly Decreases the Rate of Inhibition . . . , J.Biol.Chem., 266(23):155356–15362 (1991).
Thompson, R.C. et al., Properties, and Complete Amino Acid Sequence . . . , Proc.Natl.Acad.Sci., USA, 83:6692–6696 (1986).
McWherter, C.A. et al., Novel Inhibitors of Human Leukocyte Elastase and Cathepsin G: . . . , Biochemistry, 28:5708–5714 (1989).
Nutt, E. et al., The Amino Acid Sequence of Antistasin: . . . , J. Biol.Chem., 263((21):10162–10167 (1988).
Dunwiddie, C. et al., Antistasin, a Leech–Derived Inhibitor of Factor Xa: . . . , J.Biol.Chem., 264(26): 16694–16699 (1989).
Blankenship, D.T. et al., Amino Acid Sequence of Ghilanten: . . . , Biochem.Biophys.Res.Comm., 166(3):1384–1389 (1990).
Chapus, C. et al., Binding of Terbium . . . , J.Biol.Chem., 165(7):3726–3730 (1990).
Neurath, H. Evolution of Proteolytic Enzymes, Science, 224:350–357 (1984).
Janoff, A., Elastase in Tissue Injury, Ann.Rev.Med., 36:207–216 (1985).
Remold–O'Donnell, E. et al., Sequence and Molecular Characterization of Human Monocyte/Neurtophil Elastase Inhibitor, Proc.Natl.Acad.Sci., USA, 89:5635–5639 (1992).

*Primary Examiner*—Keith D. MacMillan
*Assistant Examiner*—T. D. Wessendorf
*Attorney, Agent, or Firm*—Darby & Darby, P.C.

[57] ABSTRACT

The present invention provides an elastase-inhibiting protein isolated ("Guamerin") from a Korean leech, Guameri (*Hirudo nipponia*) and a process for preparing the same. Guamerin is a protein of a molecular weight of 6,110 Da which is composed of 57 amino acid residues, whose active site is composed of 36-methionine and 37-isoleucine, which retains an inhibiting-activity highly specific to elastase, and which shows stability against heat as well as strong acids and alkalies. Guamerin of the present invention can be applied in the treatment of diseases associated with an excess level of elastase, such as rheumatoid arthritis, emphysema, and psoriasis.

2 Claims, 5 Drawing Sheets

NH2-Val-Asp-Glu-Asn-Ala-Glu-Asp-Thr-His-Gly-leu-Cys-Gly- 13

Glu-Lys-Thr-Cys-Ser-Pro-Ala-Gln-Val-Cys-Leu-Asn-Asn- 26

Glu-Cys-Ala-Cys-Thr-Ala-Ile-Arg-Cys-Met-Ile-Phe-Cys- 39

Pro-Asn-Gly-Phe-Lys-Val-Asp-Glu-Asn-Gly-Cys-Glu-Tyr- 52

Pro-Cys-Thr-Cys-Ala-COOH 57

ELASTASE INHIBITOR AND PROCESS FOR PREPARING THE SAME

This is a continuation of application Ser. No. 08/522,786, filed Sep. 1, 1995, now abandoned. The prior application is hereby incorporated herein by reference, in its entirety.

FIELD OF THE INVENTION

The present invention relates to a novel elastase inhibitor, more specifically, a novel protein isolated from a Korean leech, Guameri(*Hirudo nipponia*) which specifically inhibits elastase activity, and a process for preparing the same.

BACKGROUND OF THE INVENTION

Elastase is a serine protease capable of degrading mainly elastin and also connective tissue proteins such as collagen, cartilage, and fibronectin(see: Reilly, C. et al., Biochem. Biophys. Acta., 621: 147–167(1980); Mainardi, C. L. et al., J. Biol. Chem., 255: 5436–5441(1980)). Human leukocyte elastase is stored principally in neutrophils and the stored elastase is released, when neutrophils encounter foreign pathogens or antigens in blood, to degrade them so that body is protected from the harmful factors(see: Weisemann, G. et al., New Engl. J. Med., 303: 27–34(1980)).

However, uncontrolled secretion of elastase which frequently results from aging of the cells or genetic defects may cause non-specific proteolysis and trigger destructive processes associated with various chronic diseases such as rheumatoid arthritis, emphysema, and psoriasis(see: Glinski, W. et al., J. Invest. Dermatol., 75: 481–487(1980); Snider, G. L., Med. Clin. North. Am., 65: 647–666(1981)): Rheumatoid arthritis is an inflammatory disease resulting from an excessive release of elastase which causes abnormal degradation of cartilage at joints of the knee and the finger in human; emphysema is also an inflammatory disease caused by the degradative action of elastase excessively released from neutrophils which have come into the injured site of the lung tissue to prevent intrusion of pathogens from air; and, psoriasis is one of the representative skin diseases caused by elastase, which is characterized by distinct, reddish, slightly raised plaques-with adherent silvery scale.

In medical field, for the treatment of said diseases, strenuous efforts have been made in developing an agent which can effectively suppress the activity of elastase which is released abnormally in excess in the tissues of joint cartilage, lung, and skin. As a consequence, elastase-inhibiting proteins have been isolated from a variety of biological sources such as birds including turkeys or ducks, european leeches, and human skin (see: Schalwijk, J. et al., Br. J. Dermatol., 1512: 181–186(1986); Wlodow, O. et al., J. Biol. Chem., 165: 14791–14796(1990); Hochstrasser, K. et al., Hopps-Seyler's Z. Physiol. Chem., 362: 1369–1375 (1981); Seemüller, U. et al., Hopps-Seyler's Z. Physiol. Chem., 361: 1841–1846(1980)), which were found effective for the treatment of said diseases, especially when a medicine containing the protein as an active ingredient was administered directly to the affected parts.

However, the elastase-inhibiting proteins of prior art, except the one isolated from human skin, have had trouble for the use as a medicine, since their specificity for elastase is so low that the activities of other enzymes are possibly inhibited. Moreover, since the said elastase-inhibiting proteins including the one from human skin have an extremely high molecular weight, a problem has been frequently encountered that the proteins can be easily denatured by heat, which decreases their activities rapidly.

SUMMARY OF THE INVENTION

In accordance with the present invention, the inventors discovered that: a serine protease isolated from a Korean leech strongly inhibits the activity of elastase in human neutrophils in a specific manner.

The primary object of the present invention is, therefore, to provide a novel elastase-inhibiting protein(hereinafter, referred to as "Guamerin") isolated from a Korean leech, Guameri(*Hirudo nipponia*).

The other object of the invention is to provide a process for preparing the Guamerin from a Korean leech, Guameri.

BRIEF DESCRIPTION OF THE INVENTION

The above and the other objects and features of the present invention will become apparent from the following descriptions given in conjunction with the accompanying drawings, in which.

DETAILED DESCRIPTION OF THE INVENTION

Figure 1A:
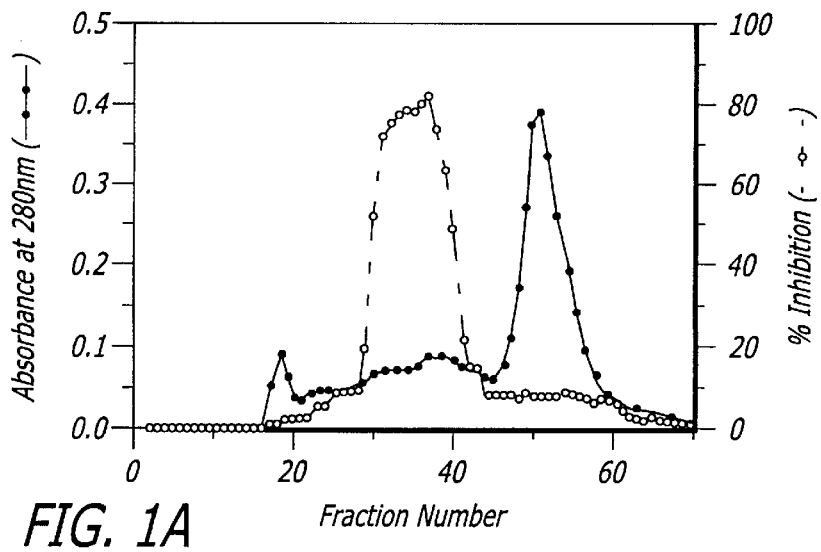
FIG. 1A represents a SEPHADEX G-75 chromatography pattern of the acetone extract of *Hirudo nipponia*.

Adult Korean leeches were collected and treated with ethyl alcohol to remove stomach impurities and blood clot. Acetone was added and homogenized, to obtain acetone extract of the leeches. The acetone extract thus obtained was concentrated, applied on a gel-filtration column, and washed, and fractions showing elastase-inhibiting activity were pooled. The active fractions, in turn, were applied on an anion-exchange column, washed, and eluted, and then fractions showing elastase-inhibiting activity were pooled again. Then, the active fractions were concentrated and applied on HPLC(high performance liquid chromatography) to isolate elastase-inhibiting protein only. A hydrophobic resin which holds hydrophobic proteins until the resin is under a hydrophillic state, was employed as a HPLC column. The elastase-inhibiting protein thus purified was named 'Guamerin' in the present invention.

Determination of the molecular weight and amino acid sequence of Guamerin revealed that the protein has a molecular weight of 6,110 Da and is composed of 57 amino acids including 10 cysteine residues which, by forming disulphide bonds, are presumed to play a crucial role in stabilizing the protein structure against heat.

On the other hand, it has been known that: all of inhibiting proteins for proteolytic enzymes (target enzymes) act as a substrate-like material(pseudo-substrate) for the target enzymes, thus decreasing the enzymatic activities; and, therefore, long-term reaction causes the hydrolysis of peptide bond of the inhibiting protein by the target enzyme, where the hydrolysed region of the protein is referred to as 'active site' of the inhibiting protein. Since the active site of the inhibiting protein confers a specificity for the target enzyme, it is very important to elucidate the structure of active site. From the point of view, the inventors determined the active site of Guamerin as 36-methionine and 37-isoleucine, which is of significance in light of the fact that: even though Guamerin has an amino acid sequence similar to those of factor Xa- or trypsin-inhibiting proteins, it only can inhibit elastase activity in a specific manner, due to the difference in their active sites(see: Nutt, E. et al., J. Biol. Chem., 263: 10162–10167(1988); Soellner, C. et al., Eur. J. Biochem., 219: 937–943(1994)).

Determination of whether Guamerin inhibits other types of proteolytic enzymes beside elastase or not, was subsequently carried out, and it was revealed that Guamerin has high specificity for the elastase. Accordingly, it is concluded that Guamerin does not affect on other types of proteolytic enzymes, thus resulting in a decrease of side effects when it is applied as a medicine.

On the other hand, it is well known that enzyme inhibitors of a lower inhibition constant(Ki) are easily dissociated from the target enzymes in a speed faster than its binding to the enzymes, indicating a more effective inhibition in a reaction involving the enzyme inhibitor with a low inhibition constant. In this regard, the fact that Guamerin whose inhibition constant of $8.1 \times 10^{-14}$ is found to be considerably low compared with that of other elastase-inhibiting proteins in the art, is meant to be an elastase-inhibiting protein with a higher activity than any other inhibitors. Moreover, it is found that the mechanism by which Guamerin inhibits elastase is a competitive inhibition.

Evaluation of the stability of Guamerin against heat and pH, presumed from the amino acid sequence and composition, indicated that the inhibiting protein is quite stable against heat as well as strong acids and alkalies. Accordingly, these properties of Guamerin work in favor of industrialization with a negligible loss which may often result from denaturation in the processes of mass production, storage, and transport.

Guamerin of the present invention can be applied in the treatment of diseases associated with an excess level of elastase, such as rheumatoid arthritis, emphysema, and psoriasis. The genetic information deduced from the amino acid sequence of Guamerin can be also employed in a mass production employing genetic engineering techniques known in the art.

In describing the amino acid sequence of protein in the present invention, one-letter symbols abbreviated by the IUPAC-IUB standard are employed as followings:

| Amino acid | Symbol |
| --- | --- |
| Alanine | A |
| Arginine | R |
| Asparagine | N |
| Aspartic acid | D |
| Cysteine | C |
| Glutamine | Q |
| Glutamic acid | E |
| Glycine | G |
| Histidine | H |
| Isoleucine | I |

-continued

| Amino acid | Symbol |
| --- | --- |
| Leucine | L |
| Lysine | K |
| Methionine | M |
| Phenylalanine | F |
| Proline | P |
| Serine | S |
| Threonine | T |
| Tryptophan | W |
| Tyrosine | Y |
| Valine | V |

The present invention is further illustrated in the following examples, which should not be taken to limit the scope of the invention.

EXAMPLE 1

Purification of Guamerin

Fully matured leeches collected at Chonju, a southern city of Korea, were employed in the purification process regardless of their size, if they were clearly identified as Korean leech, i.e., Guameri(*Hirudo nipponia*), in light of their back patterns and colours. About 100 leeches weighing 40 g in total were treated with 100 ml of 95% ethyl alcohol(4° C.) to anaesthetize and remove stomach impurities and blood clot. Leeches were washed thoroughly with deionized water and put in 200 ml of 80% acetone(−20° C.) before homogenized in an automated mixer. Then, NaCl and TCA (trichloroacetic acid) were added to the final concentrations of 0.3 M and 0.2 M, respectively, to extract proteins. To concentrate the acetone extract thus prepared, four volumes of 100% acetone(−20 ° C.) were added and left at −20 ° C. for 1 hour to form light grey precipitate, which was subjected to a centrifugation and an evaporation of residual acetone subsequently, to obtain pure light grey powder.

The acetone extract powder was dissolved in Tris-HCl buffer solution(pH 8.0) containing 200 mM NaCl (hereinafter referred to as "Buffer A") and then applied on a SEPHADEX G-75 gel filtration column(110×2 cm; Sigma, USA) preequilibrated with Buffer A at a flow rate of 1 ml/min, and fractions showing the elastase-inhibiting activity were pooled(see: FIG. 1A).

Figure 1B:
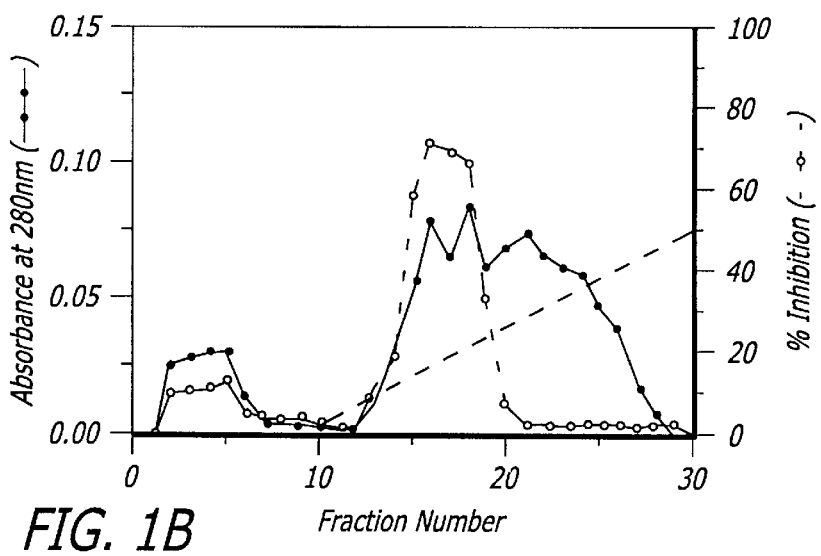
FIG. 1B represents a DEAE-SEPHAROSE chromatography pattern of the eluent from the SEPHADEX G-75 chromatography.

The active fractions were dialysed against another Tris-HCl buffer solution(pH 8.0, hereinafter referred to as "Buffer B") to remove NaCl completely and then applied on a DEAE-SEPHAROSE column(6×1.3 cm; Sigma, USA) preequilibrated with Buffer B at a flow rate of 0.5 ml/min. Elution was made with a linear NaCl gradient from 0 mM to 400 mM, and elution of Guamerin having elastase-inhibiting activity was identified at a peak at the NaCl gradient from 120 mM to 150 mM(see: FIG. 1B).

Figure 1C:
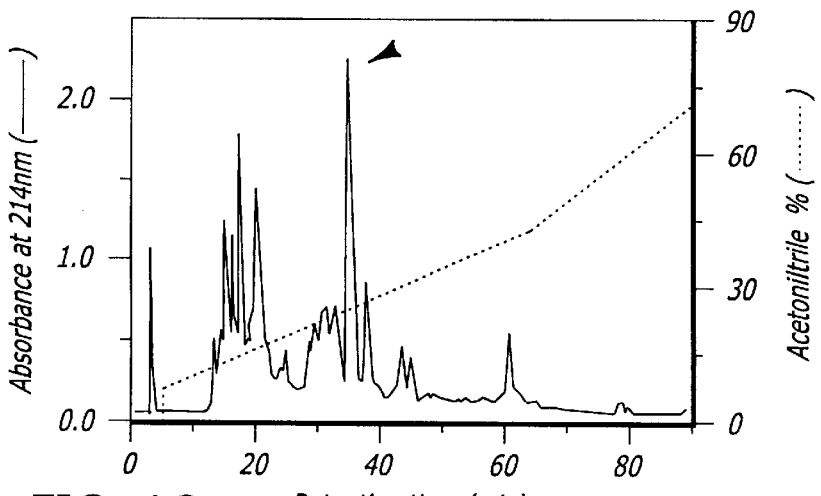
FIG. 1C represents a HPLC(high performance liquid chromatography) pattern of the eluent from the DEAE-SEPHAROSE chromatography.

The active fractions obtained from said DEAE-SEPHAROSE chromatography were pooled, dialysed against Buffer B to remove NaCl completely, concentrated and applied on HPLC column(30×0.39 cm, Delta-pak C18, Millipore, USA) preequilibrated with 0.1% trifluoroacetic acid at a flow rate of 1 ml/min. Elution of pure Guamerin (arrow head) was made with a linear acetonitrile gradient from 25%(v/v) to 60%(v/v) and a peak at 35 min of retention time was identified as Guamerin(see: FIG. 1C).

The activity of the purified Guamerin was assayed as follows: 50 μl of elastase-containing solution(0.37 mg/ml) and 500 μl of 1 mM ρ-nitroaniline were mixed together, and 50 μl of each of fractions obtained in the course of purification was added to the mixture, and left to react at 37° C. for 50 min. The absorbance(O.D.) at 440 nm calculated in terms of the hydrolysed ρ-nitroaniline, was measured. O.D. values of the control and the active fractions were compared, and the activity of Guamerin was determined, based on the decrease in ρ-nitroaniline degradating activity of elastase.

Purification of Guamerin are summarized in Table 1 below. Protein was quantitatively assayed by Bradford method(see: Bradford, M. M., Anal. Biochem., 72: 248–254 (1976)). In this regard, one unit(1 U) was defined as the amount of inhibitor that decreases the degradation of 1 μM ρ-nitroaniline by elastase per minute.

TABLE 1

Purification of Guamerin

| Purification step | Total protein (mg) | Specific activity (units/mg) | Yield (%) |
| --- | --- | --- | --- |
| Acetone extract | 2000 | 0.94 | 100 |
| SEPHADEX G-75 | 16.1 | 95 | 82 |
| DEAE-SEPHAROSE | 2.7 | 273 | 39 |
| HPLC | 0.7 | 361 | 19 |

As shown in Table 1, the specific activity of purified Guamerin was determined as 361 units/mg and the yield was 19%.

EXAMPLE 2

Determination of Molecular Weight of Guamerin

Figure 2:
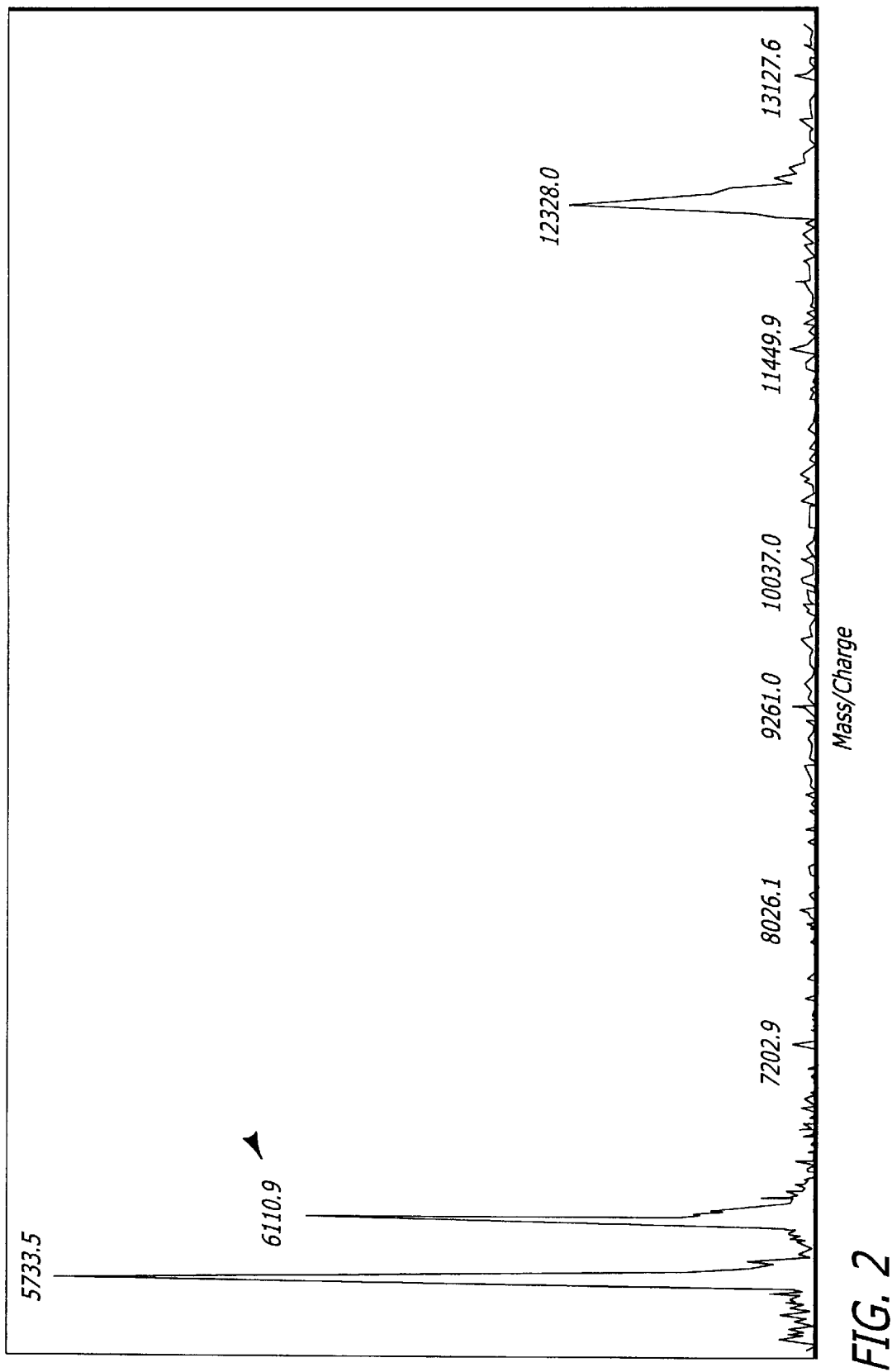
FIG. 2 is a mass spectrum of Guamerin of the present invention analyzed by a MALDI(matrix-assisted laser desorption ionization) mass spectrometry.

By the aid of MALDI(matrix-assisted laser desorption ionization, Kompact, MALDI II, Kratos, UK) mass spectrometry, Guamerin was determined as a protein having a molecular weight of 6,110 Da(see: FIG. 2).

EXAMPLE 3

Determination of Amino Acid Sequence and Active Site of Guamerin

Figures 3, 5:
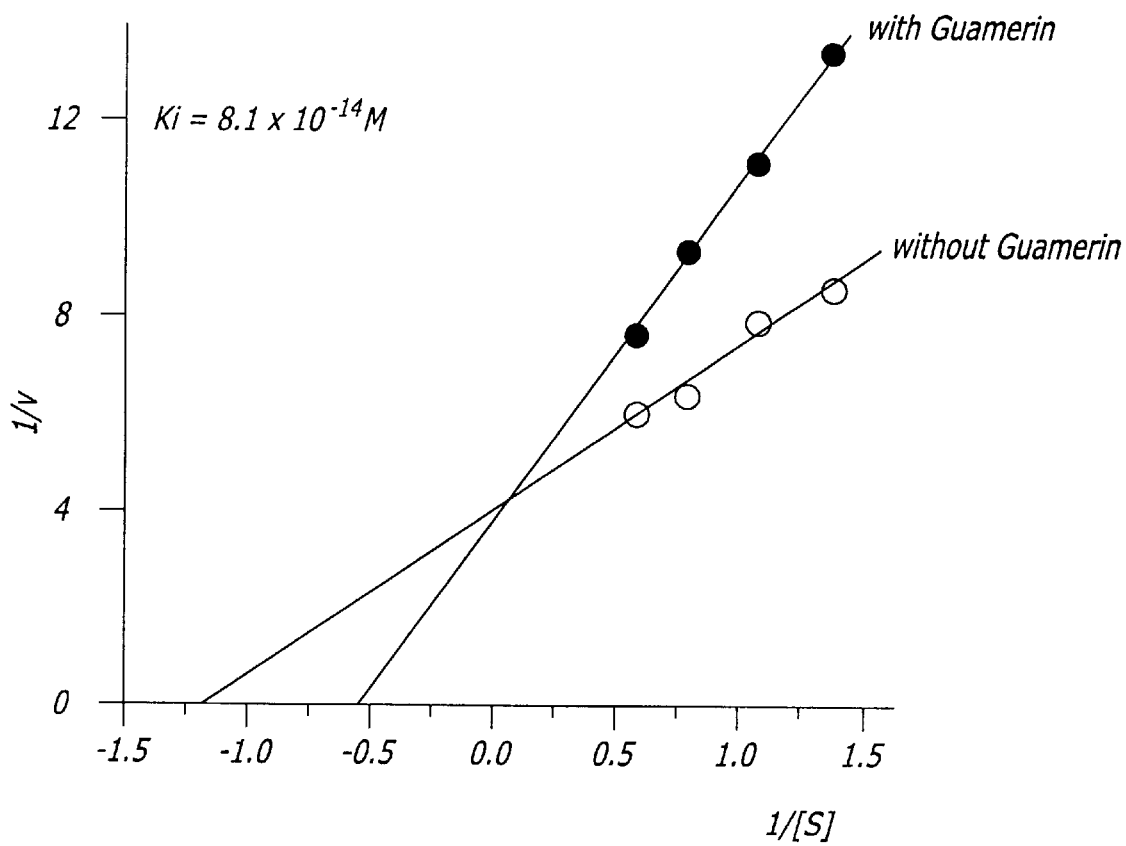
FIG. 3 is the amino acid sequence of Guamerin.
FIG. 5 is a graph for the determination of inhibition constant of Guamerin.

The amino acid sequence of Guamerin prepared in Example 1 was determined by employing an amino acid sequence analyzer(Applied Biosystems 476A protein sequencer, USA) (see: FIG. 3). As shown in FIG. 3, it was found that Guamerin is comprised of total 57 amino acid residues, which contains 10 cysteine residues. In addition, comparison of amino acid sequences between Guamerin and elastase-inhibiting proteins of prior art confirmed that Guamerin of the present invention is a novel protein.

On the other hand, to elucidate the active site of Guamerin, it was reacted with elastase for 48 hours, and the amino acid sequence of its N-terminus was determined using an amino acid sequence analyzer. As a result, it was determined that: the peptide bond between 36-methionine and 37-isoleucine was hydrolysed; and, therefore, the active site of Guamerin includes 36-methionine and 37-isoleucine.

EXAMPLE 4

Specificity of Inhibiting Activity of Guamerin

Figure 4:
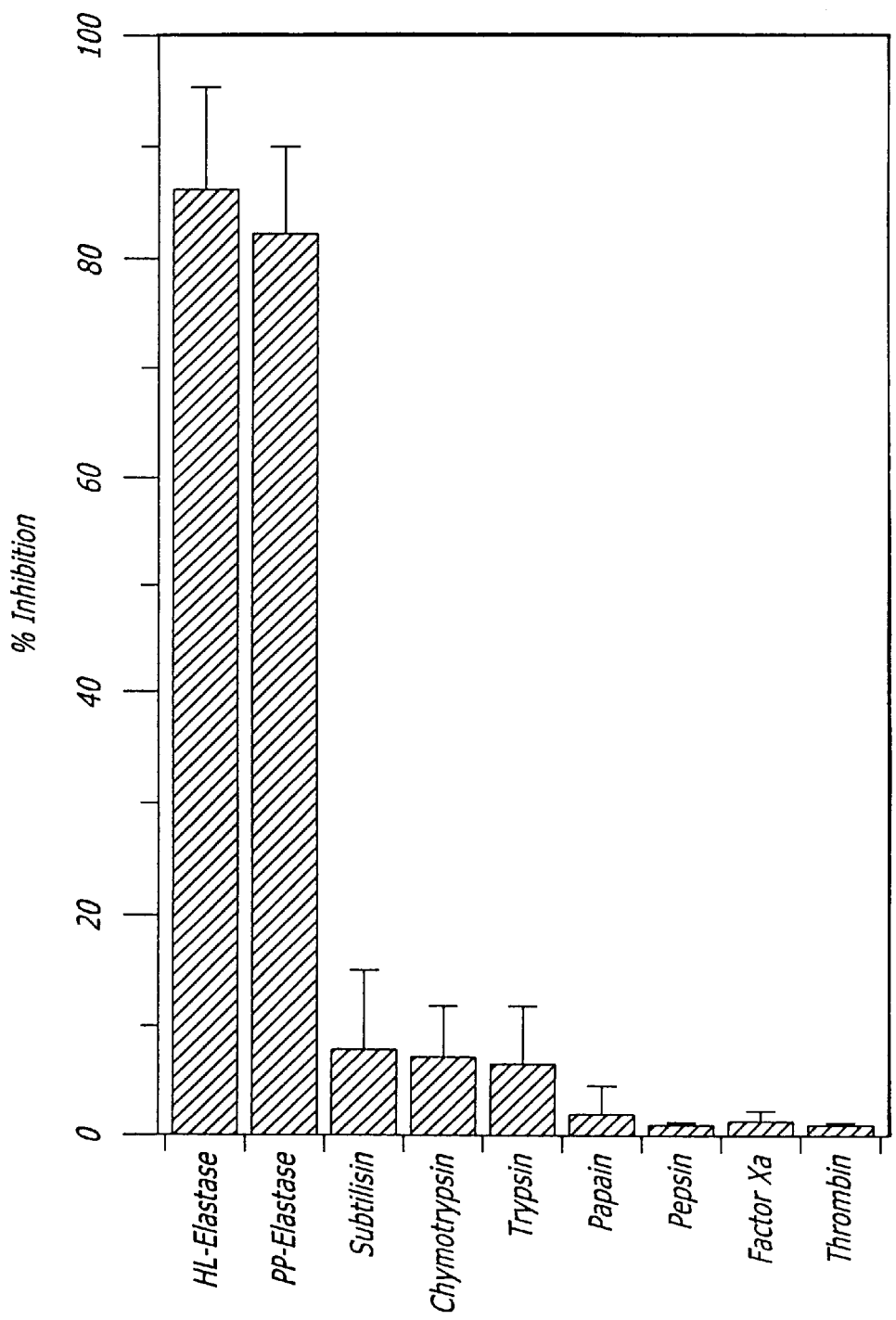
FIG. 4 is a graph showing the specificity of Guamerin.

The specific activities of Guamerin on the other types of proteases beside elastase, were studied; and, it was determined that: while it has no effect on papain, pepsin, thrombin, and factor Xa, Guamerin had about 15% of inhibiting-activity against trypsin, chymotrypsin, and subtilisin. The said activity of Guamerin is, however, extremely low, compared to about 90% of activity on elastase, suggesting that Guamerin is highly specific for elastase(see: FIG. 4). In FIG. 4, HL-elastase and PP-elastase represent the ones isolated from human leukocyte and porcine pancreas, respectively.

On the other hand, the inhibition constant of Guamerin which was obtained by employing elastase as a substrate was determined as $8.1 \times 10^{-14}$M, which was considerably low compared with those of other elastase-inhibiting proteins in the prior art, such as eglin $C(10^{-10}-10^{-11}$ M) isolated from human skin or elafin($6 \times 10^{-10}$ M) isolated from european leeches. As a result, it is found that Guamerin is of a higher inhibition activity than any other elastase-inhibiting proteins known in the art. Moreover, as shown in FIG. 5, it was clearly confirmed that: Guamerin inhibits the elastase activity in a competitive manner, since Guamerin competes with the substrate for elastase in the binding to the target enzyme, i.e., elastase.

EXAMPLE 5

Evaluation of Stability of Guamerin

Figure 6:
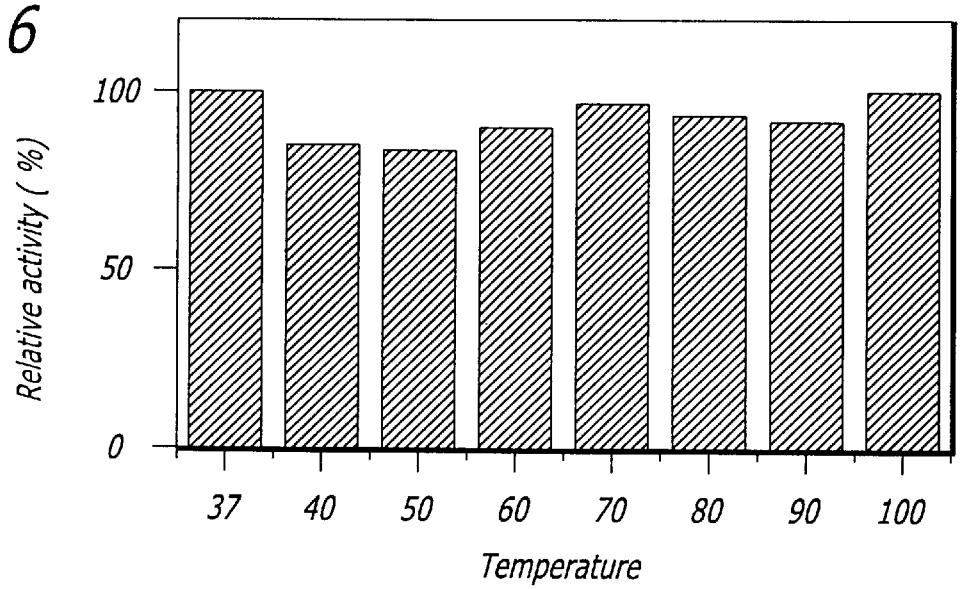
FIG. 6 is a graph showing the heat-stability of Guamerin.

To investigate the effect of heat on the activity of Guamerin, it was subjected to heating condition at an interval of 10° C. ranging from 40° C. to 100° C. for 15 min(see: FIG. 6). As a result, there was no change in the activity of Guamerin, suggesting that the protein is very stable to heat shock.

Figure 7:
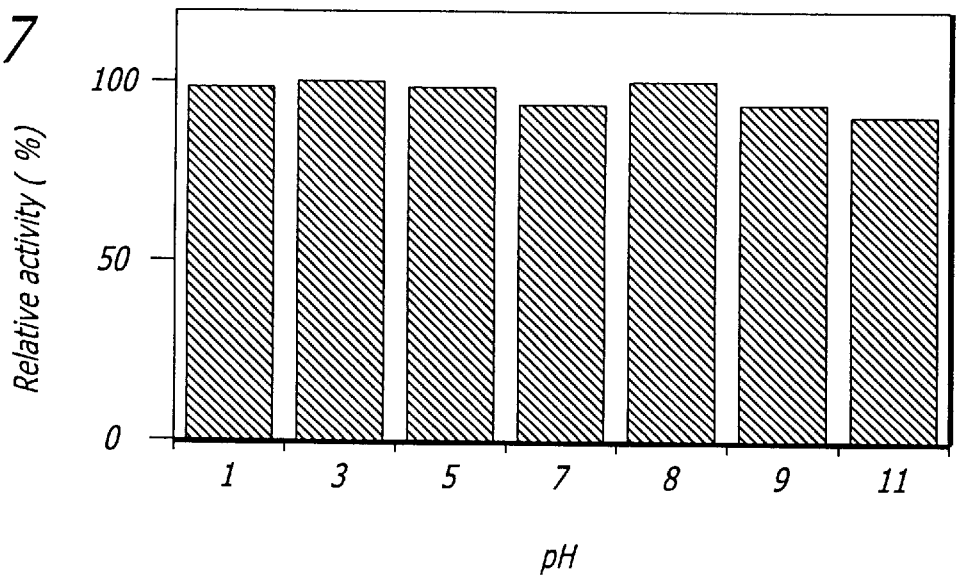
FIG. 7 is a graph showing the pH-stability of Guamerin.

Further, to examine if strong acids or alkalies influence the activity of Guamerin, it was treated with solutions ranging from pH 1 to pH 11 at an interval of pH 2 for 15 min(see: FIG. 7). As a result, there was also no change in the activity of Guamerin, suggesting that the protein is also very stable to strong acids and alkalies.

As clearly demonstrated and explained above, the present invention provides an elastase-inhibiting protein isolated ("Guamerin") from a Korean leech, Guameri(*Hirudo nipponia*) and a process for preparing the same. Guamerin of the present invention can be applied in the treatment of diseases associated with an excess level of elastase, such as rheumatoid arthritis, emphysema, and psoriasis.

What is claimed is:

1. An elastase-inhibiting protein (Guamerin) of 6,110 Da, isolated from a Korean leech, Guameri (*Hirudo nipponia*) which is represented as SEQ ID NO:1:

V D E N A E D T H G L C G E K T C S P A

Q V C L N N E C A C T A I R C M I F C P

N G F K V D E N G C E Y P C T C A.

2. The elastase-inhibiting protein (Guamerin) of claim 1, wherein an active site consists of 36-methionine and 37-isoleucine.

* * * * *